United States Patent [19]
Birch et al.

[11] Patent Number: 5,840,171
[45] Date of Patent: Nov. 24, 1998

[54] ELECTROCHEMICAL REACTIONS

[75] Inventors: Brian Jeffrey Birch, Northants; Nicholas Andrew Morris, Bedford, both of Great Britain

[73] Assignee: Unilever Patent Holdings BV, Vlaardingen, Netherlands

[21] Appl. No.: 464,715
[22] PCT Filed: Dec. 21, 1993
[86] PCT No.: PCT/GB93/02615
§ 371 Date: Nov. 3, 1995
§ 102(e) Date: Nov. 3, 1995
[87] PCT Pub. No.: WO94/15207
PCT Pub. Date: Jul. 7, 1994

[30] Foreign Application Priority Data

Dec. 23, 1992 [GB] United Kingdom ............ 9226840

[51] Int. Cl.⁶ .............. C25B 15/02; C25B 1/24; C25B 1/16; C25C 1/00
[52] U.S. Cl. .......... 205/335; 205/498; 205/510; 205/633; 205/778; 205/792.5; 205/793
[58] Field of Search .............. 205/335, 510, 205/498, 633, 778, 793, 792.5

[56] References Cited

U.S. PATENT DOCUMENTS

| | | | |
|---|---|---|---|
| 3,623,960 | 11/1971 | Williams | 204/1 T |
| 4,127,448 | 11/1978 | Schick et al. | 204/1 T |
| 4,129,478 | 12/1978 | Racine et al. | 204/1 T |
| 4,832,797 | 5/1989 | Vadgama et al. | 204/1 T |
| 4,863,571 | 9/1989 | Chambaere | 204/1 T |
| 4,919,767 | 4/1990 | Vadgama et al. | 204/153.1 |
| 4,935,105 | 6/1990 | Churchouse | 204/153.12 |
| 5,059,290 | 10/1991 | Uchiyama | 204/153.1 |
| 5,230,783 | 7/1993 | Scortichini et al. | 204/153.12 |
| 5,352,348 | 10/1994 | Young et al. | 204/153.12 |

FOREIGN PATENT DOCUMENTS

| | | |
|---|---|---|
| 30195 | 6/1981 | European Pat. Off. . |
| 170375 | 2/1986 | European Pat. Off. . |
| 2394802 | 1/1979 | France . |
| 1098653 | 1/1968 | United Kingdom . |
| 1601985 | 11/1981 | United Kingdom . |
| 87/06702 | 11/1987 | WIPO ................... 205/778 |
| 91 15758 | 10/1991 | WIPO . |

OTHER PUBLICATIONS

Hawkridge, et al: "Indirect Coulometric Titration of Biological Electron Transport Components", Analytical Chemistry, vol. 445, No. 7, Jun. 1973–pp. 1021–1027.

Olthuis, et al: "Simplfied design of the coulometric sensor-actuator system by the application of a time–dependent actuator current", Sensors and Actuators B Chemical, vol. B7, No. 1/3, Mar. 31, 1992, pp. 479–483.

Cox, James A. et al, "Voltammetric Ion Selective Electrode for the Determination of Nitrate", Analytical Chemistry, Apr. 1979, pp. 554–556.

Primary Examiner—Kathryn L. Gorgos
Assistant Examiner—Chrisman D. Carroll
Attorney, Agent, or Firm—Pillsbury Madison & Sutro LLP

[57] ABSTRACT

The invention provides an electrochemical reaction wherein a controlled amount of a first reagent is generated electrochemically at an electrode in electrical contact with a solution of an electrochemically inert salt, comprising applying a suitable electrical potential to the electrode for a suitable time to generate a controlled amount of the first reagent by electrochemical reaction between the electrode and a species in solution producing a localized thin layer environment comprising the first reagent in the vicinity of the electrode; and monitoring the amount or presence of the first reagent or a further species produced in solution in response to production of the first reagent. The method invention thus involves generating the first reagent in situ at an electrode. Diffusion of the reagent in solution surrounding the electrode will result in creation of a localized environment of the reagent in the vicinity of the electrode, with the amount of reagent depending on the generating current and the length of time for which it is applied, and so being readily and easily controllable.

25 Claims, 3 Drawing Sheets

ELECTROCHEMICAL REACTIONS

This is a national stage application of PCT/GB93/02615, filed Dec. 21, 1993.

FIELD OF INVENTION

This invention concerns electrochemical reactions.

BACKGROUND TO THE INVENTION

There are circumstances involving electrochemical reactions when it is necessary to provide a particular environment, e.g. alkaline conditions, for a reaction of interest to take place, or in which a particular reagent, e.g. hydrogen ions, is required to participate in a reaction of interest. Hitherto this has generally been achieved by supplying an appropriate reagent to the reaction mixture, e.g. by depositing a releasable layer of reagent within an electrochemical cell or by supplying reagent in solution to the cell. Practical difficulties can arise in certain situations. For example it can be difficult to deposit more than one layer of reagent in such a way that all layers are efficiently released into solution. Further, supplying a measured or known quantity of reagent in solution requires appropriately accurate measurement. The present invention provides an alternative approach.

SUMMARY OF THE INVENTION

In one aspect the present invention provides an electrochemical reaction, wherein a controlled amount of a first reagent is generated electrochemically at an electrode in electrical contact with a solution of an electrochemically inert salt, comprising applying a suitable electrical potential to the electrode for a suitable time to generate a controlled amount of the first reagent by electrochemical reaction between the electrode and a species in solution producing a localized thin layer environment comprising the first reagent in the vicinity of the electrode; and monitoring the amount or presence of the first reagent or a further species produced in solution in response to production of the first reagent.

The term "thin layer" as used in this specification means having a thickness less than 1 mm, preferably in the range 0.1 to 0.2 mm.

The method of the invention thus involves generating the first reagent in situ at an electrode. Diffusion of the reagent in solution surrounding the electrode will result in creation of a localized environment of the reagent in the vicinity of the electrode, with the amount of reagent depending on the generating current and the length of time for which it is applied, and so being readily and easily controllable.

Reagent generated by this approach can be used in two main ways:

1) To provide a suitable environment to enable a desired reaction to take place, e.g. to provide an alkaline environment prior to electrochemical measurement of reducing sugar content of a solution, as disclosed in the specification of British Patent Application No. 9325189.0. In this case the concentration of reagent within the localized environment is not critical. It is merely sufficient that a specified minimum concentration is provided or exceeded.

2) To provide a known amount of a reagent which reacts stoichiometrically with an analyte, e.g. hydrogen ions for use in a pH titration measurement. In this case it is necessary to provide a precise known amount of reagent at known time.

These two ways could also be used together, with the first reagent providing a necessary environment and reacting stoichiometrically.

The first reagent may comprise hydrogen ions or hydroxyl ions. These are readily produced by application of an electrical potential to water, e.g. an aqueous solution of a reactant. Depending on the polarity of charge at an electrode, water is broken down according to the following equations:

Anode

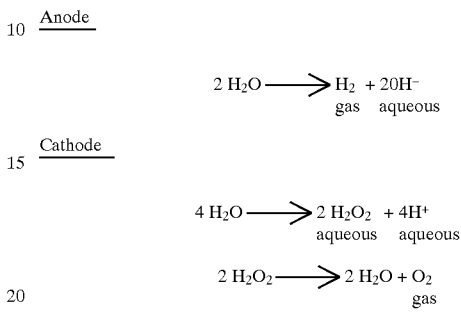

Cathode $$4 H_2O \longrightarrow 2 H_2O_2 + 4H^+$$
$$\text{aqueous} \quad \text{aqueous}$$

$$2 H_2O_2 \longrightarrow 2 H_2O + O_2$$
$$\text{gas}$$

Thus, at the anode hydroxyl ions are produced together with hydrogen gas, while at the cathode hydrogen ions are produced together with oxygen gas.

Other reagents, such as chlorine, bromine, and iodine, can alternatively be produced as the first reagent, by treatment of suitable salt solutions, e.g. KCl, KBr, KI.

The first reagent may be used to generate a further reagent to create a desired environment or participate in a desired reaction. For example, by covering, the electrode with an ion-exchange membrane containing an ion of interest, reagent such as EDTA can be expelled from the membrane in response to contact with hydroxyl ions generated at the electrode.

It may be important to prevent agitation or mixing of solution in the vicinity of the electrode at which reagent is produced. Some electrochemical reactions producing the first reagent also involve the production of gas, as in the production of hydrogen ions or hydroxyl ions, and in these cases it may be necessary to take steps to prevent the generation or release of the gas or to nullify the effect of the gas in solution. For example, the effects of gas can be nullified by locating a layer of porous material over the electrode. The porous material can be porous paper, such as blotting paper, porous ceramic material, porous ion exchange material, porous dielectric material, porous polymer etc. Certain of these materials can conveniently be applied by screen printing over the electrode, or by in situ polymerisation, e.g. initiated by exposure to UV light. In the case of hydrogen gas, its concentration in solution can be reduced by employing palladium electrodes, as this material absorbs hydrogen.

In the case of oxygen gas, its evolution can be prevented by employing a sacrificial metal anode, for example of silver, lead or zinc. Other approaches may also be possible.

The invention finds particular application in measurements on thin layers of reagent, constrained within impervious barriers, e.g. capillary fill devices (CFDs) or narrow bore tubes with diameters of thin layer dimensions but unspecified length. It is well known to use CFDs for electrochemical measurements, e.g. as disclosed in EP 0170375A. A typical CFD comprises two plates separated by a gap sufficiently small that liquid can be drawn into it by capillary action. The gap is generally less than 1 mm, preferably in the range 0.1 to 0.2 mm. The internal faces of the plates carry electrodes, e.g. deposited by screen printing, for making electrochemcial measurements. In a CFD or narrow bore tube, the plate spacing or tube bore will constrain the extent of the localized environment in the vicinity of the electrode in one dimension (generally perpendicular to the electrode surface). The extent of the localized environment in other dimensions (generally parallel to the electrode surface, i.e. in a lateral direction) will depend on the extent of the electrode and the rate of lateral diffusion of the first reagent in solution. It is found in practice in a CFD that lateral diffusion is generally slow, typically being of the order of 1 mm in 120 seconds. Lateral diffusion can also be controlled if required by use of a guard electrode, as described in the specification of British Patent Application No. 9325189.0.

The thin layer environment can also be defined by interstices or recesses, e.g. pores, wells or channel of thin layer dimensions, in solid matrices e.g. of paper, gels, (water soluble or insoluble), polymers, ion exchange membranes etc. Such thin layer environments may be in contact with bulk solution, e.g. with one or more wells formed in suitable matrix material located in a bulk solution container, thus enabling effective generation of one or more localized thin layer environments in communication with bulk solution, so that diagnostic reactions, etc. can be performed within the thin layer environment.

The localized thin layer environment may be used in isolation, e.g. in the case of CFDs and narrow bore tubes containing sample. Alternatively, the thin layer environment may be employed in conjunction with bulk solution, e.g. with a tube or test strip defining a thin layer environment dipping into bulk solution, or as with recesses in a bulk solution container as discussed above.

The electrode should be inert with respect to reactants involved in reactions taking place, so no undesired side reactions occur. Suitable electrode materials include gold, platinum, palladium, silver, carbon, carbon/silver, porous conducting ceramic materials, electrically conducting polymeric substances, e.g. polypyrrole.

The electrochemically inert salt provides inert ions which function as charge carriers during the process. Suitable salts include salts of sodium, potassium, lithium, ammonium etc, with potassium salts generally being favoured currently. The anionic component may be, for example, nitrate, sulphate, chlorate, perchlorate, fluoroborate, etc. Potassium sulphate, potassium chlorate and sodium nitrate are currently favoured salts. The salt will typically be in aqueous solution and possess a sufficiently high oxidation/reduction potential so as not to take part in the electrochemical process.

Suitable electrical potentials and times will depend on the conditions and reactions involved, and can be readily determined in any given case. As an example, for a measurement in a CFD application of a current of 3 mA for about 60 seconds or less might be suitable.

Depending on the reactions involved, it may be appropriate to monitor the first reagent, a further species produced in solution in response to production of the first reagent, or both of these.

For example, the first reagent may particpate in an electrochemical reaction, so by monitoring depletion of the first reagent an indication is obtained of the extent of reaction.

Production of the first reagent may also be exploited in flow measurement, by generating a pulse of first reagent at known time in a flowing solution and monitoring at a downstream detector the time interval between generation of the pulse and arrival of the pulse at the detector, thus providing a measure of the rate of flow of the solution. In this case, monitoring takes place at a location remote from the electrode where the first reagent is produced. In cases involving static rather than flowing solutions it would generally be appropriate for monitoring to take place in the vicinity of the reagent-producing electrode.

In cases where the first reagent enables a reaction to take place or particpates in a reaction, by monitoring a product of the reaction an indication is obtained of the progress of the reaction.

Monitoring may be effected directly or indirectly, and may be qualitative or quantitive.

A variety of different monitoring techniques may be employed, involving monitoring of a range of properties of the solution. For example the appearance, e.g. color or cloudiness, of the solution may be monitored using colorometric, spectrophotometric or turbidometric techniques. Electrochemical monitoring is a particularly convenient approach, and potentiometric or coulometric (e.g. amperometric) techniques can be used as appropriate, with appropriate techniques being selected as a matter of design choice. An internal electrochemical reference system can readily be provided in known manner, e.g. in a CFD, by a suitable reference electrode such as a silver/silver chloride electrode.

As will be apparent from the above, the invention may be embodied in several forms, including a CFD and in devices designed to be used with bulk solution. The technique may also be useful for the local generation of acid or alkali conditions in bulk solution containing some analyte requiring pH manipulation. The advantage of this embodiment over existing techniques is that acidification/alkalinisation of the entire solution is not necessary, resulting in significant cost advantages.

The invention may also be exploited for the measurement of laminar flow rates inside tubes. The tube need not necessarily be of thin layer diameter: in wider bore tubes laminar flow may result in a thin layer of flowing medium (constituting a thin layer environment) being present adjacent the tube side wall. A pulse of reagent e.g. alkali/acid may be generated at some point upstream of a detector, and the time between generation and detection may be used to calculate flow rates. In a suitable embodiment this technique may also be used to reduce the bio-fouling of tubes, by generating hydrogen ions to decomplex any trace metal ions in solution. This technique has particular applications in the sewage and waste-water treatment industries. Provided adequate mixing of the solution at some point down-stream of the pulse occurs, the microflora in the reactors should not be affected as there is no net pH change.

The invention may also have a particular application for the performance of pH-titrations, especially in a flow-injection analysis system (FIA). There is a fixed and simple relationship between the number of coulombs of charge passed through a solution and the number of moles of $OH^-$ and $H^+$ generated. As the reactions within a CFD occur in a controlled volume environment, the concentration of alkali or acid may be ascertained. For example by employing stepped pulses of charge and intermittently or continuously measuring the potential, the concentration of analyte may be determined. An auto-titrator employing such a system would have advantages over existing system in terms of a reduction of reagent costs, and in the volume of sample required.

BRIEF DESCRIPTION OF THE DRAWINGS

The invention will be further described, by way of illustration, with reference to the accompanying drawings, in which.

DETAILED DESCRIPTION OF THE DRAWINGS

Figure 1:
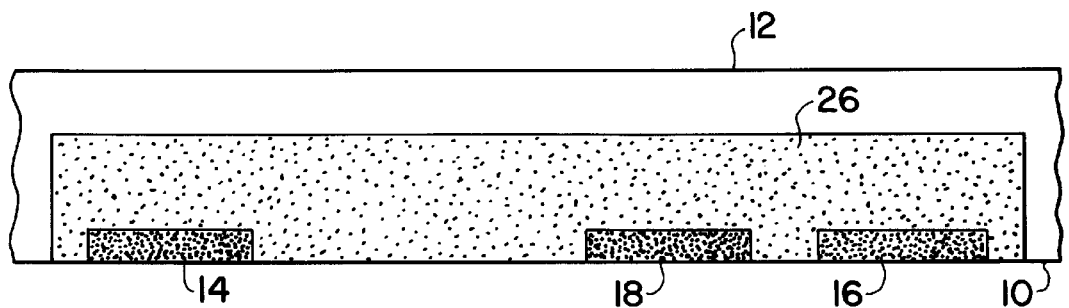
FIG. 1 is a schematic cross-sectional view of a CFD in accordance with the invention.
Figure 2:
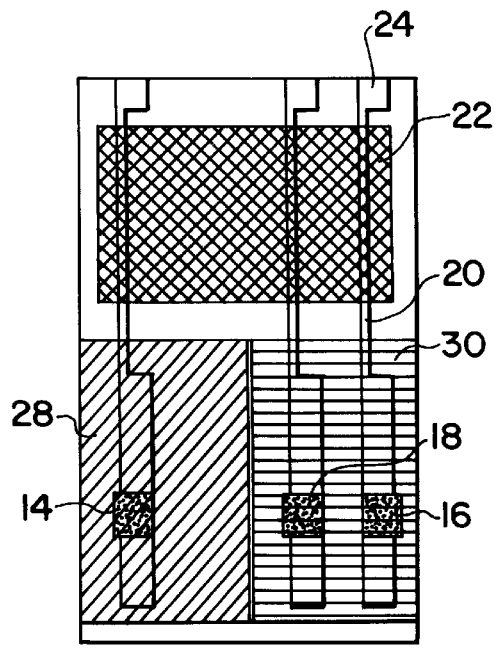
FIG. 2 is a plan view of the CFD of FIG. 1 on a reduced scale.

FIGS. 1 and 2 illustrate schematically a CFD in accordance with the invention and its use in generating localized acid and alkali environments, e.g. for use in determining the concentration of reducing sugar in a test solution.

The CFD is generally of conventional construction, e.g. as described in EP 0170375 A. The CFD comprises two spaced apart plates 10 and 12, e.g. of glass, ceramic or plastics material, separated by a gap of about 0.1 mm. The lower plate 10 carries 3 electrodes: an acid generator gold electrode 14, an alkali generator gold electrode 16, and a sliver/silver chloride reference electrode 18. The electrodes are deposited using conventional screen printing techniques. Conductors 20 extending through a dielectric layer 22 (shown in FIG. 2 by cross-hatching) connect the electrodes to respective contact or terminal pads 24.

A porous layer 26 (for clarity not shown in FIG. 2) is deposited on top of the electrodes to prevent agitation or mixing of solution in the CFD on production of gas bubbles at the electrodes. In production embodiments, it is envisaged a layer of porous ceramic or ion exchange material will be screen printed over the electrodes.

The apparatus finds application, for example, in determining the concentration of reducing sugar in a test solution, using the technique as described in the specification of British Patent Application No. 9325189.0.

In a series of experiments, determinations were made of fructose in a solution containing sodium nitrate (1M) and potassium chloride (50 mM). The sodium nitrate constitutes the electrochemically inert salt, and the potassium chloride provides a source of chloride ions for a Ag/AgCl reference electrode. The experiments were carried out using a CFD generally as described in connection with FIGS. 1 and 2.

A potential difference was applied between electrodes 14 and 16. This resulted in generation of hydrogen ions and oxygen gas at electrode 14 (the cathode) and hydroxyl ions and hydrogen gas at electrode 16 (the anode), in accordance with the equations given above. During the reaction, the hydrogen ions and hydroxyl ions diffuse slowly from the generator electrodes, creating a localized acidic zone 28 (shown by diagonal lines in FIG. 2) in the porous layer in the vicinity of electrode 14 and a localized alkali zone 30 (shown by horizontal lines in FIG. 2) in the porous layer in the vicinity of electrode 16. These zones are separated by a neutral boundary approximately mid-way between the electrodes, so that the zones are mutually exclusive and in equilibrium.

The alkali zone 30 constitutes a suitable environment in which fructose (or other reducing sugars) can have a reducing effect, reducing available reducible reagents. In the present examples, oxygen present in the system was used as the electron acceptor for the oxidation of fructose.

The resulting reducing reaction was monitored by measuring the potential at the hydroxyl producing electrode 16 by use of the reference electrode 18. Electrode 18 was thus located within the alkali zone 30.

In a series of experiments, during an initial period of 130 seconds a current of 3 mA was applied to electrodes 14 and 16. The potential difference between the reference electrode 18 and the alkali-generator/sensor electrode 16 was recorded over the total duration of each trial. Thereafter the driving potential between the 'acidic' & 'alkali' electrodes 14 and 16 was terminated and the potential in the region of the alkali electrode 16 relative to the reference electrode 18 was measured for a further 130 seconds. The equilibrium potential is some function of the change in chemical potential. Two replicates each of solutions containing 0.5M fructose and no fructose were used. In addition each solution carried 50 mM potassium chloride and 1M sodium nitrate, as noted above.

Figure 3:
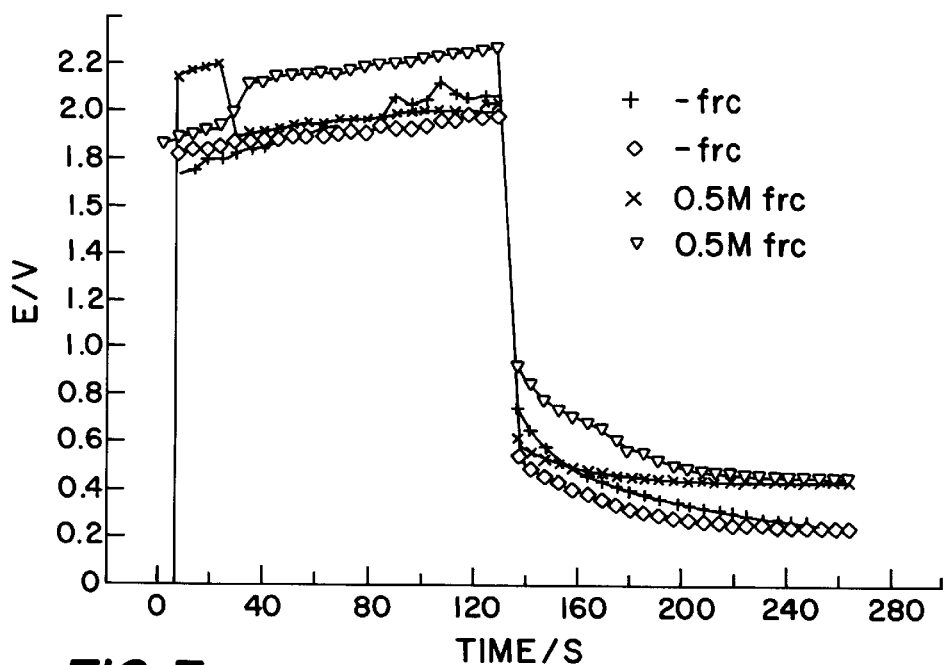
FIG. 3 is a graph of potential difference versus time obtained using the CFD of FIGS. 1 and 2, with different concentrations of fructose in solution.
Figure 4:
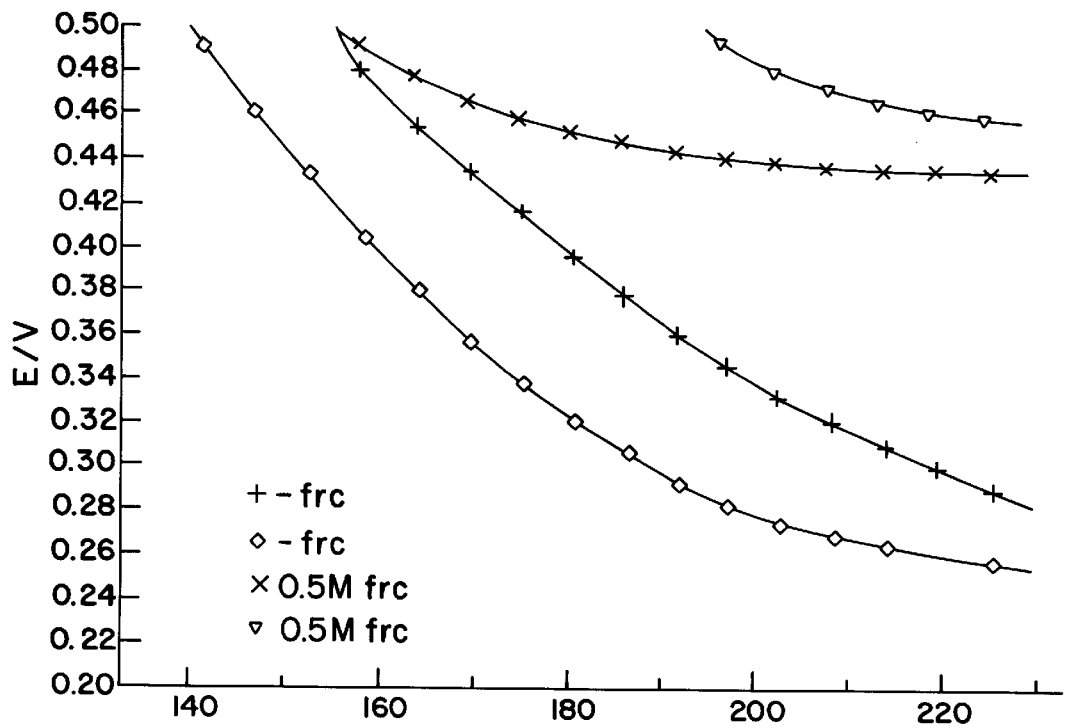
FIG. 4 is an enlarged scale version of the end portions of the curves of FIG. 3.

The results are shown in FIGS. 3 and 4.

Figure 5:
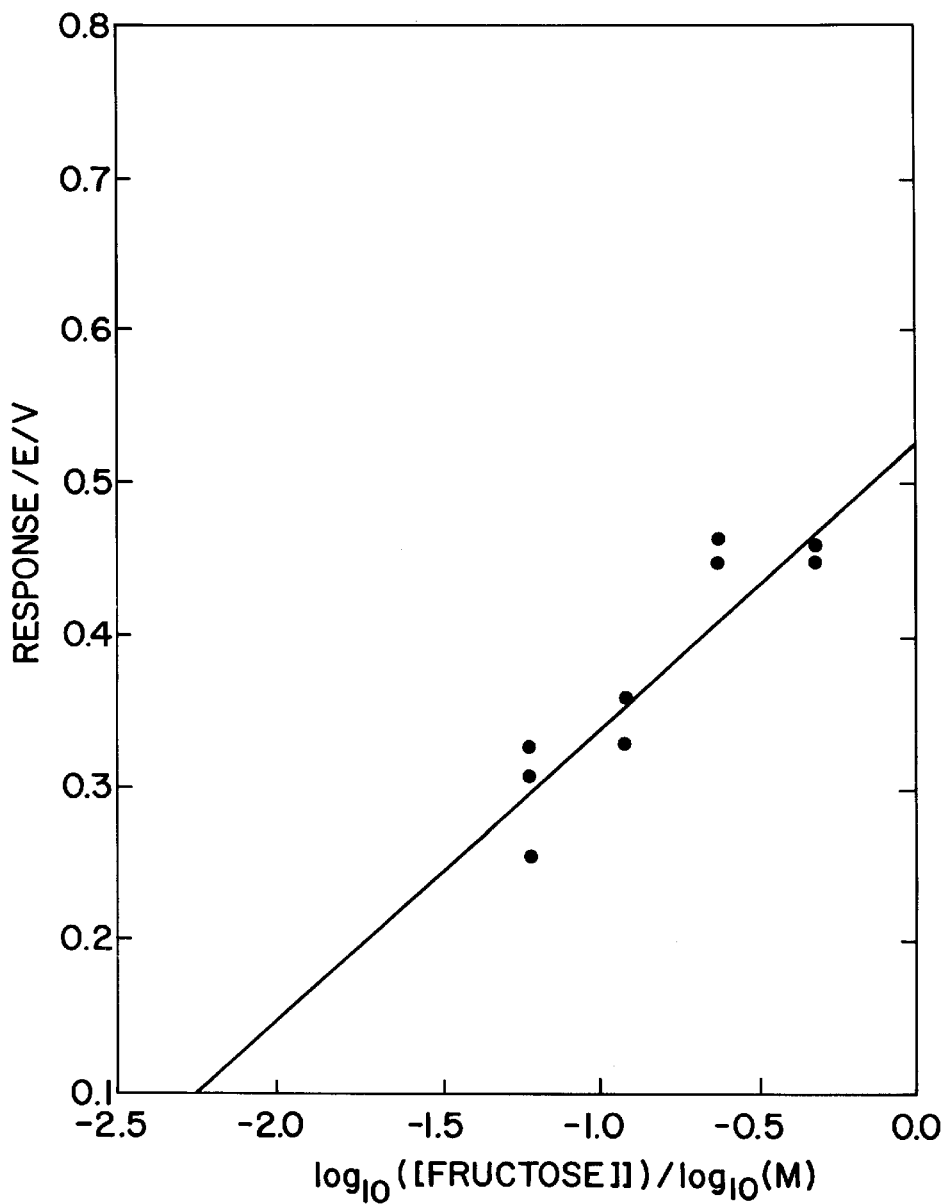
FIG. 5 is a graph of final potential versus log fructose concentration obtained from graphs such as FIG. 4.

FIG. 5 is a plot of further results obtained in generally similar manner, demonstrating a clear (logarithmic) correlation between fructose concentration and final potential. FIG. 5 shows the potential response curve at various concentrations of fructose (0.5M, 0.25M, 0.125M, 0.0612M) using electro-generation of hydroxyl ions. Conditions: total charge passed 0.24 C (4 mA over 60 s), reaction time 60 s: total analysis time 120 s. Points plotted show electrogenerated reagent/printed Au electrode (response=0.52+0.18 (log [fructose]). Linear regression lines are shown for data obtained by electro-generated reagent and for the response obtained using lithium hydroxide to facilitate fructose oxidation.

It is to be noted that these are preliminary results obtained in non-optimised conditions. Various parameters can be altered to improve performance, including:

a) maximization of electrode area in order to minimise current density, b) minimization of volume of accessible solution, reducing the amount of time required to attain a certain concentration of $H^+/OH^-$.

The CFD of FIGS. 1 and 2 can alternatively be used in pH titrations. In this case, the potential between electrodes 14 and 16 is applied in short pulses, with the resulting potential of electrode 16 (and hence change in pH in the vicinity of that electrode) being measured by use of reference electrode 18 between each pulse. By plotting the measured potential versus applied charge, a characteristic sigmoidal curve is obtained, in which the point of inflection indicates the point of neutrality. Such a reaction can be readily carried out under the control of suitable computer control means, desirably programmed to vary the size of applied pulses depending on the circumstances, reducing the pulse size as the end point of neutrality is approached for enhanced accuracy.

In an alternative embodiment for pH titration, charge can be applied continuously and the effect monitored continuously, rather than in pulsed manner, by use of separate, independent charging and monitoring circuits.

Figure 6:
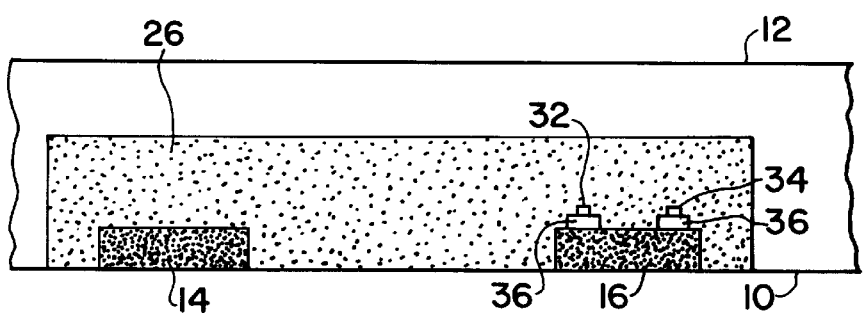
FIG. 6 is a schematic cross-sectional view of a modification of the embodiment of FIGS. 1 and 2.

In one convenient arrangement, illustrated schematically in FIG. 6, in place of reference electrode 18 of FIGS. 1 and 2, one of the generator electrodes, say alkali generator 16, carries a pair of sensor electrodes 32, 34 on its upper surface, separated from that surface by respective dielectric layers 36. The sensor pair conveniently comprises a gold electrode 32 and a silver/silver chloride electrode 34. Porous layer 26 covers all the electrodes.

In use, charge is applied continuously between electrodes 14 and 16, and the resulting potential difference between electrodes 32 and 34 is continuously monitored in an independent circuit. A characteristic sigmoidal curve is again obtained.

The method of the invention may, for example, be used to determine the ripeness of fruit and vegetables. This would involve measuring the fructose (and other reducing sugars) content of liquor expressed from a fruit or vegetable sample, e.g. as described above.

We claim:

1. An electrochemical process for generating a controlled amount of a reagent electrochemically which comprises providing an electrode in electrical contact with a solution of an electrochemically inert salt, wherein the solution comprises a thin layer thereof of thickness less than 1 mm, creating an electric potential at the electrode for a sufficient time to generate by electrochemical process between the electrode and a component of the solution a controlled amount of the reagent in a localized region of the thin layer adjacent the electrode, and monitoring the presence and amount of the reagent in the localized region, said reagent being generated at known time in a flowing solution and being monitored on arrival at a downstream detector to provide a measure of the rate of flow of the solution.

2. A process according to claim 1, wherein the reagent comprises hydrogen ions or hydroxyl ions.

3. A process according to claim 1, wherein the reagent comprises chlorine, bromine, or iodine.

4. A process according to claim 1, wherein gas produced at the electrode is absorbed in a layer of porous material located over the electrode.

5. A process according to claim 1, wherein the electrochemically inert salt comprises a salt of sodium, potassium, lithium or ammonium.

6. A process according to claim 1, wherein the electrochemically inert salt comprises a nitrate, sulphate, chlorate, perchlorate or fluoroborate.

7. A process according to claim 1, wherein the electrochemically inert salt comprises potassium sulphate, potassium chlorate or sodium nitrate.

8. A process according to claim 1, wherein the electrochemically inert salt is in aqueous solution.

9. A process according to claim 1, wherein the reagent is monitored electrochemically.

10. A process according to claim 9, wherein electrochemical monitoring is carried out using an internal electrochemical reference system.

11. A process according to claim 1, forming part of a pH titration.

12. A process according to claim 1, forming part of electrochemical measurement of reducing sugar content of a solution.

13. An electrochemical process for generating a controlled amount of a reagent electrochemically which comprises providing an electrode in electrical contact with a solution of an electrochemically inert salt, wherein the solution comprises a thin layer thereof of thickness less than 1 mm, creating an electric potential at the electrode for a sufficient time to generate by electrochemical process between the electrode and a component of the solution a controlled amount of the reagent in a localized region of the thin layer adjacent the electrode, producing a further component in solution responsive to production of the reagent, and monitoring the presence and amount of the further component in the localized region, said further component being generated at a known time in a flowing solution and being monitored on arrival at a downstream detector to provide a measure of the rate of flow of the solution.

14. A process according to claim 13, wherein the electrode is covered with an ion-exchange membrane containing an ion of interest which is expelled from the membrane in response to contact with the reagent generated at the electrode, said ion of interest constituting the further component.

15. A process according to claim 13, wherein the reagent comprises hydrogen ions or hydroxyl ions.

16. A process according to claim 13, wherein the reagent comprises chlorine, bromine, or iodine.

17. A process according to claim 13, wherein gas produced at the electrode is absorbed in a layer of porous material located over the electrode.

18. A process according to claim 13, wherein the electrochemically inert salt comprises a salt of sodium, potassium, lithium or ammonium.

19. A process according to claim 13, wherein the electrochemically inert salt comprises a nitrate, sulphate, chlorate, perchlorate or fluoroborate.

20. A process according to claim 13, wherein the electrochemically inert salt comprises potassium sulphate, potassium chlorate or sodium nitrate.

21. A process according to claim 13, wherein the electrochemically inert salt is in aqueous solution.

22. A process according to claim 13, wherein the further component is monitored electrochemically.

23. A process according to claim 22, wherein electrochemical monitoring is carried out using an internal electrochemical reference system.

24. A process according to claim 13, forming part of a pH titration.

25. A process according to claim 13, forming part of electrochemical measurement of reducing sugar content of a solution.

* * * * *